United States Patent
Shen

(10) Patent No.: US 11,033,722 B1
(45) Date of Patent: Jun. 15, 2021

(54) AURICULAR DRUG DELIVERY SYSTEM

(71) Applicant: Pathway Innovations and Technologies, Inc., San Diego, CA (US)

(72) Inventor: Ji Shen, San Diego, CA (US)

(73) Assignee: Sorrento Technology Holdings, Las Vegas, NV (US)

( * ) Notice: Subject to any disclaimer, the term of this patent is extended or adjusted under 35 U.S.C. 154(b) by 20 days.

(21) Appl. No.: 15/969,732

(22) Filed: May 2, 2018

Related U.S. Application Data

(60) Provisional application No. 62/500,342, filed on May 2, 2017.

(51) Int. Cl.
*A61M 31/00* (2006.01)

(52) U.S. Cl.
CPC ......... *A61M 31/00* (2013.01); *A61M 2202/03* (2013.01); *A61M 2205/581* (2013.01); *A61M 2209/088* (2013.01); *A61M 2210/0662* (2013.01)

(58) Field of Classification Search
CPC ............ A61M 31/00; A61M 2205/581; A61M 2202/03; A61M 2209/088; A61M 2210/0662
See application file for complete search history.

(56) References Cited

U.S. PATENT DOCUMENTS

| | | | |
|---|---|---|---|
| 8,328,830 B1 * | 12/2012 | Pandit | A61M 3/0212 606/162 |
| 2016/0354559 A1 * | 12/2016 | Gavini | A61M 15/0085 |

FOREIGN PATENT DOCUMENTS

| | | | |
|---|---|---|---|
| DE | 14200105 | * | 12/2014 |
| DE | 102017104167.2 | * | 2/2017 |

* cited by examiner

*Primary Examiner* — Bhisma Mehta
*Assistant Examiner* — Daniel Moore
(74) *Attorney, Agent, or Firm* — Insigne PC

(57) ABSTRACT

A device for auricularly delivering and/or receiving medication which comprises an earcup, a drug cartridge or drug reservoir having active ingredients, and a fluid generator that generates a fluid having active ingredients and delivers the fluid to the earcup. A method for auricularly delivering medication which comprises the steps of receiving medication from a cartridge at a fluid generator, generating fluid comprising the medication, and passing the fluid to an earcup. A system for auricularly delivering medication comprising a headphone comprising at least one earcup, and a replaceable and consumable drug cartridge coupled to the headphone. A method for receiving medication which comprises the steps of placing an earcup on an ear, operating a headphone coupled to the earcup, and receiving fluid generated by a fluid generator, the fluid comprising active ingredients, wherein the fluid generator receives medication from a cartridge comprising active ingredients.

33 Claims, 2 Drawing Sheets

AURICULAR DRUG DELIVERY SYSTEM

CROSS-REFERENCE TO RELATED APPLICATIONS

The present application claims priority to U.S. Provisional Patent Application No. 62/500,342, filed on May 2, 2017 entitled, "Auricular Drug Delivery System," the disclosure of which is herein incorporated by reference in its entirety.

BACKGROUND OF THE INVENTION

1. Field of Invention

The present disclosure relates to drug delivery and, more specifically, to a system and method for delivering a drug via the ear.

2. Description of Related Art

Ear candling, also called ear coning or thermal-auricular therapy, is an alternative medicine practice claimed to improve general health and well-being. Typically, the technique involves lighting one end of a hollow candle and placing the other end in the ear canal. Particularly, one end of a cylinder or cone of a waxed cloth wick is lit, and the other end is placed into the patient's ear. The flame is cut back occasionally with scissors and extinguished between five to ten centimeters from the patient. In some applications, the patient is lying on one side, having the vertically oriented candle placed into the treated ear. The candle can be held through a shield, such as a paper plate or aluminum pie tin, to protect against any hot wax or ash falling onto the patient. Another way to perform ear candling involves the patent lying on their back, face up, with the ear candle extending out to the side with a forty-five-degree upward slant. A dish of water may be placed next to the subject under the treated ear. The flame is thought, by proponents of such treatments, to create negative pressure, drawing wax and debris out of the ear canal, which appears as a dark residue. An ear candling session can last from 15 minutes to 45 minutes, during which time a series of one or two ear candles may be applied to each ear.

The widespread enthusiasm supporting ear candling originates from ancient Egyptians, Mayans, and Tibetans as having practiced ear candling. Typical claims include removal of cerumen (ear wax), reduction of sinus pressure, treatment of allergies, treatment of hearing loss, sharpening of the senses of smell, taste and color perception, relief of temporomandibular joint (TMJ) pain, and the treatment of vertigo, among others. Proponents of ear candling claim oxygen is drawn from the flame, thus producing a vacuum that pulls residue out of the ear. Many proponents further claim the vacuum affects and drains all passages of the head via the tympanic membrane (ear drum).

Medical research has shown that the practice is both dangerous and ineffective and does not help remove earwax or toxicants. Using a lit candle in the proximity of a patient's face carries a high risk of causing potentially severe skin/hair burns and middle ear damage. Additionally, the use of wax has its own risks and concerns. Ear candling increases the risk of starting a fire; burns to the face, ear canal, eardrum, and middle ear; injury to the ear from dripping wax; ears plugged by candle wax; bleeding; and puncturing the eardrum.

Moxibustion is an acupuncture technique involving moxa, the herb mugwort (*Artemisia vulgaris*). In Traditional Chinese Medicine (TCM), this herb is used to invigorate the flow of Qi ("chi," in TCM, it is the energy that keeps one from falling ill, the energy that forces one's heart to beat, or cells to divide) and blood, promote a pain-relieving effect, and deeply penetrate the area of discomfort with soothing warmth. In moxibustion, the moxa herb is ignited and can either be placed on top of a needle (Needle Moxa); applied without the use of needles, as it can be burned in stick form as the acupuncturist hovers and swirls the stick of burning moxa above various acupuncture points; or the moxa can be indirectly placed on various acupoints on the body using a thin slice of ginger or other barrier to shield the skin. Proponents of moxibustion claim it is effective for cases including tight muscle spasms, low back pain, frozen shoulder, or various osteoarthritic joint pains, especially when pain is worsened by damp and cold weather. Moxibustion has also been purported to ease ear pain and ear infections when applied near the ear. Like ear candling, use of a lit moxa stick in the proximity of a person's face carries a high risk of causing potentially severe skin/hair burns.

Therefore, what is needed is an apparatus, system, and method for auricularly delivering medication to a patient without the risks associated with open flames. This need has heretofore remained unsatisfied.

SUMMARY OF THE INVENTION

The present disclosure overcomes these and other deficiencies of the prior art by providing device, method and system for auricularly administering and receiving medication. In an exemplary embodiment of the present disclosure, a device is used to auricularly deliver medication having an earcup, a drug cartridge or drug reservoir comprising active ingredients, and a fluid generator, wherein the fluid generator generates a fluid comprising the active ingredients and delivers the fluid to the earcup. In another embodiment, the device may further comprise a sound emitter configured to deliver sound to the earcup.

In another embodiment, the fluid generator may further comprise a vaporizer. In another embodiment, the fluid generator further comprises a humidifier. In another embodiment, the humidifier may be an ultrasonic humidifier, a boiling humidifier, a mechanical humidifier, and a combination thereof. In another embodiment, the fluid generator may further comprise a nebulizer. In another embodiment, the device may further comprise a headband. In another embodiment, the device may further comprise a controller to control the fluid generator's rate of generation of the fluid. In another embodiment, the drug cartridge may be replaceable.

In another exemplary embodiment of the present disclosure, a system for auricularly delivering medication includes a headphone comprising at least one earcup and a replaceable and consumable drug cartridge configured to be coupled to the headphone. In another embodiment, the headphone may further comprise a fluid generator coupled to the drug cartridge, wherein the fluid generator generates a fluid comprising active ingredients obtained from the drug cartridge. In another embodiment, the fluid generator may further comprise a vaporizer. In another embodiment, the fluid generator may further comprise a humidifier. In another embodiment, the humidifier may be one of an ultrasonic humidifier, a boiling humidifier, a mechanical humidifier, and/or a combination thereof. In another embodiment, the fluid generator may further comprise a nebulizer.

In another exemplary embodiment of the present disclosure, a method for auricularly delivering medication includes receiving, at a fluid generator, medication from a cartridge; generating, at the fluid generator, fluid comprising the received medication; and passing the fluid to an earcup. In another embodiment, the method may further comprise the step of placing the earcup adjacent to a patient's ear such that the patient's ear is completely encapsulated by the earcup. In another embodiment, the fluid generator comprises a vaporizer. In another embodiment, the fluid generator comprises a humidifier. In another embodiment, the humidifier is selected from the group consisting of: an ultrasonic humidifier, a boiling humidifier, a mechanical humidifier, and a combination thereof. In another embodiment, the fluid generator comprises a generator comprises a nebulizer. In another embodiment, the method may further comprise the step of regulating, at a controller, the fluid generator's rate of generation of the fluid. In another embodiment, the vaporized medication is passed to the earcup by an impeller. In another embodiment, the method may further comprise the step of delivering, to the earcup, sound generated from a speaker.

In another exemplary embodiment of the present disclosure, a method for receiving medication includes placing an earcup on an ear; operating a headphone coupled to the earcup, the headphone comprising a fluid generator; and receiving, at the ear, fluid generated by the fluid generator, the fluid comprising active ingredients; wherein the fluid generator receives medication from a cartridge comprising active ingredients. In another embodiment, the method may further comprise the step of receiving sound from a sound emitter coupled to the headphone. In another embodiment, the fluid generator may comprise a vaporizer. In another embodiment, the fluid generator may comprise a humidifier. In another embodiment, the humidifier may comprise an ultrasonic humidifier, a boiling humidifier, a mechanical humidifier, and/or a combination thereof. In another embodiment, the headphone may comprise a headband. In another embodiment, the method may further comprise the step of controlling, at a controller operatively connected to the fluid generator, the fluid generator's rate of generation of the fluid. In another embodiment, the method may further comprise the step of coupling, the cartridge to the fluid generator, the earcup, or the headphone. In another embodiment, the cartridge may be detachably coupled to the fluid generator, the earcup, or the headphone.

The foregoing, and other features and advantages of the invention, will be apparent from the following, more particular description of the preferred embodiments of the invention, the accompanying drawings, and the claims.

BRIEF DESCRIPTION OF THE DRAWINGS

For a more complete understanding of the present disclosure, the objects and advantages thereof, reference is now made to the ensuing descriptions taken in connection with the accompanying drawings briefly described as follows.

DETAILED DESCRIPTION OF EMBODIMENTS

Figure 1:
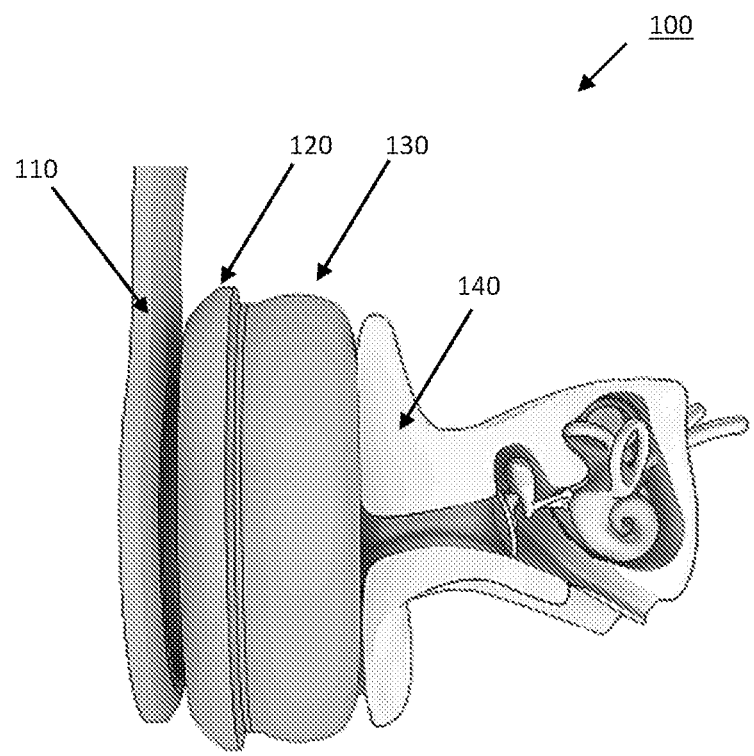
FIG. 1 illustrates perspective view of an auricular medication delivery device depicting an earcup place next to a patient's ear, according to an exemplary embodiment of the present disclosure.

Further features and advantages of the invention, as well as the structure and operation of various embodiments of the invention, are described in detail below with reference to the accompanying FIGS. 1-2, wherein like reference numerals refer to like elements. Although the invention is described in the context of a headphone form factor, any type of form factor that covers one or both ears of a patient's head may be implemented, without departing from the embodiments contemplated herein.

In an exemplary embodiment of the present disclosure and with reference to FIG. 1, an auricular drug delivery system (or "headphone") 100 according to an embodiment of the invention. As used throughout this disclosure, the use of the term "headphone" is to denote shape, not necessarily whether it provides audio such as music or speech. However, the contemplated embodiments may also supply audio stimulation, such as music, noise-cancellation, "white noise," or other sounds without departing from the embodiments contemplated. Thus, in addition to providing a system and method for auricularly delivering medication to a patient, the contemplated embodiments may further include conventional audio components, e.g., speakers, drivers, wireless communication devices, and/or audio cables, the identification and implementation of which are apparent to one of ordinary skill in the art. The headphone 100 comprises a headband 110, housing 120, and earcup 130. The headband 110 extends (not shown) over the user's head in order to securely wear the headphone 100. Additionally, the headband 110 may be configured in any way such that an earcup 130 may be held over or near one or both of a patient's ear or ears.

Optionally, the headband 110 may include a second housing (not shown) and earcup (not shown) at its opposite end (proximate to the user's other ear), which may be identical to housing 120 and earcup 130. The housing 120 and/or the headband 110 may house the auricular drug delivery components. The earcup 130 is preferably any soft and/or pliable material, conducive of comfort, the identification of which is apparent to one of ordinary skill in the art, to cover and be comfortably worn on or near the patient's ear 140. In an embodiment of the invention, the earcup 130 comprises padding or a flexible material that when placed over a patient's ear 140, forms a fluid seal or near fluid seal able to prevent medication from escaping the patient's ear and the inner space of the ear cup.

Figure 2:
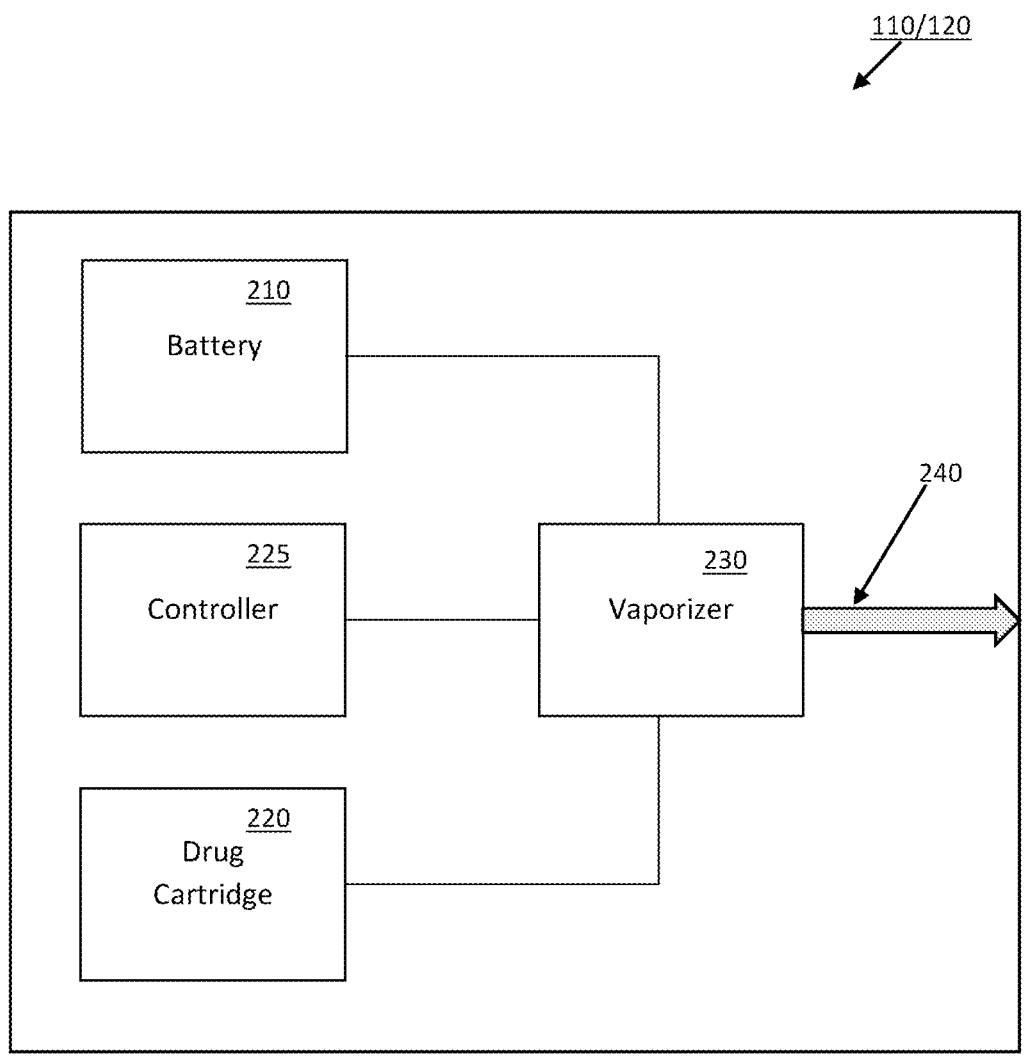
FIG. 2 illustrates a diagram showing functional element of an auricular medication delivery system, according to an exemplary embodiment of the present disclosure.

In another exemplary embodiment of the present disclosure and with reference to FIG. 2, auricular drug delivery components within the housing 120 and/or headband 110 are illustrated. Particularly, the housing 120 may comprise a battery 210, a drug cartridge 220, a controller 225, a vaporizer 230, and a drug delivery channel 240. The battery 210 supplies power to the relevant components, such as the controller 225 and vaporizer 230. In an alternative embodiment, the battery 210 may be replaced or supplemented by an external power source (not shown). The controller 225 is operatively connected to and controls the operation of various components such as the vaporizer 230 and may perform functions including, but not limited to, on/off, and intensity. The controller 225 may also control audio output, when so configured. For example, the controller 225 may be coupled to an on/off switch (not shown) and an intensity adjuster such as a knob, switch, and/or slider (not shown). The vaporizer 230 vaporizes active ingredients in a solid, fluid, liquid, and/or gel material(s) provided by the drug cartridge 220. In an embodiment of the invention, the drug cartridge 220 is a disposable cartridge that can be removed and replaced. Additionally, more than one drug cartridge 220 may be used to deliver multiple drugs simultaneously. Alternatively, the housing 120 comprises a fluid reservoir (not shown) for holding active ingredients. The fluid reservoir can supplement or replace the drug cartridge 220.

It is to be understood that the battery 210, drug cartridge 220, controller 225, vaporizer 230, and drug deliver channel 240 can be located anywhere with the headband 110, housing 120, and earcup 130. For example, these components 210-240 can be all located within the earcup 130, all located within the headband 110, all located within the housing 120, or spread across the headband 110, housing 120, and/or earcup 130 in any manner.

The vaporizer 230 may utilize any method of heating, including conduction, convection, and/or radiation, or any combination thereof. For example, in an embodiment utilizing conduction heating, the material in the cartridge 220 is heated by being in contact with a heating element. In convection, heated air is passed across the material in the cartridge 220 to heat the cartridge 220. In either embodiment, the contents of the cartridge 220 is vaporized without combustion.

In another embodiment, the vaporizer 230 may be replaced by a humidifier. The humidifier may use, for example, a metal diaphragm vibrating at an ultrasonic frequency, to create mist. Such an ultrasonic humidifier is usually silent, and also produces a cool mist from a liquid cartridge 220. Alternatively, the humidifier may implement a rotating disc, e.g., impeller or propeller, that moves the contents of the cartridge 220 to a diffuser. The diffuser breaks the liquid into fine droplets that float into the air. In another embodiment, the humidifier boils the liquid and releases the active ingredients from the cartridge 220 via steam. Implementation of a diffuser in the manner contemplated is readily apparent to one skilled in the art.

In another embodiment of the present disclosure, the vaporizer 230 may be replaced with a nebulizer that, for example, uses oxygen, compressed air, and/or ultrasonic power to break up a solution or suspension from the cartridge 220 into small aerosol droplets, to deliver medication to the patient.

A vaporizer, nebulizer, or humidifier are exemplary types of fluid generators. Fluid is referred to herein as any type of gas or liquid, or combination of gas and liquid that comprises active ingredients for delivery to the patient's ear 140.

The drug delivery channel 240 delivers the vaporized contents of the cartridge 220, once misted, vaporized, or nebulized, to the user's ear 140. The active ingredients can be any type of medicinal substance, such as, but not limited to mugwort, gentamicin, brain-derived neurotrophic factor (BDNF), neurotrophins-3, N-acetyl cysteine, growth factor, neomycin, dexamethasone, dextran, rhodamine, and tetrahydrocannabinol.

The amount and duration of drug administration are critical for some treatments. Future treatments may require the delivery of combinations of drugs in a timed and sequenced manner to be effective, and these requirements will not easily be met with systemic delivery. Therefore, the present invention's "cartridge concept" provides a solution to support the dynamic dosing amounts needed and the timing requirements of the delivery. If the system 100 includes an audio speaker, instructions may be provided to the user regarding the timing of doses and the switching of cartridges.

The present disclosure may be utilized in many areas. For example, the present disclosure may be utilized in sleep-related treatments. Sleep-related ailments may include Restless Leg Syndrome, in inability to enter rapid eye movement (REM) sleep, insomnia, etc. The present disclosure may also treat comorbidity associated with insomnia, such as depression and a change in hormones (and resulting weight gain and stress hormone levels and infertility). Depending on the active ingredients, the present invention may also treat anxiety, pain, depression and other affective disorders, adverse symptoms of chemotherapy, stress, chronic fatigue syndrome, Lyme disease, hormonal imbalance, immuno deficiencies, infertility, tinnitus or other hearing problems, obesity, neuro-development problems, and other diseases that result in significant decrease in energy and increase in sleepiness/tiredness.

The present disclosure may further help to elevate the patient's mood and improve wellbeing, boost the immune system, fight off colds and bacterial infections, menstrual issues, improve circulation and urine output, relieve headaches and digestion problems, improve quality of life, particularly for people with chronic health conditions, alleviate the pain associated with intravenously injected medication and treatments, improve sleep for people who are hospitalized and who receive long term infusion treatments, and reduce pain for children undergoing procedures such as tonsillectomy.

The present disclosure may further address the disadvantages with using essential oils without a delivery system, which include the amount, purity, potency (where the container is not properly stored) and the messy/cumbersome delivery of the oils. In such an application, the cartridge 220 will solve the timing, amount and potency issue by encapsulating the oil in sealed capsule and ensure it is sealed after every application.

The present disclosure also provides convenience for those who will use it while travelling. Embodiments of the present disclosure are compliant with TSA regulations on what can be brought onto a plane. In some embodiments, the cartridge 220 may be inflammable, thereby preventing a potential environmental hazard.

In an embodiment of the present disclosure, the system 100 also includes a "cleaning track cartridge" that would be used after a number of uses. The user will be reminded because the new cartridge will not be usable unless the system is cleaned. In an embodiment, the controller 225 may provide three warnings before the cartridge will not be used unless the device is cleaned. The warning may be conveyed to the user though a visual or audio indicator.

In clinical settings, the present disclosure may be used in conjunction with other drug delivery apparatuses. For example, it can assist patients undergoing chemotherapy/radiotherapy and infusion treatments with managing the side effects including nausea and patients with other side effects during dialysis or post-transplant treatments. In addition to an improved quality of life, the present disclosure improves compliance and adherence (and ultimately treatment outcomes) for patients who often are discontinue treatment due to severe side effects—which can be up to 50% of the treatment population.

In addition, auricular delivery is non-systemic and will therefore avoid disturbing the entire body and therefore improve the side effect profile. Furthermore, the present disclosure also provides patients with sensitive or dry skin an alternative to topical treatments that may irritate the already delicate skin and even avoid rashes or allergic reactions. The non-systemic and non-topical nature of the present disclosure provides alternatives to patients that allow them to continue treatment, as opposed to discontinuing treatment due to severe side effects.

Although an auricular medication apparatus and method is shown and described, auricular medication systems may be implemented according to other embodiments of the disclosure. For example, the headband may be configured to hold the earcup on the patient's ear using a band that traverses the circumference of the patient's head. Additionally, the earcup may be held on or over the patient's ear by a device that is not affixed to the patient's head. In such an embodiment, the earcup may simply be held against the patient's head by the patient resting their head on the earcup. Alternatively, the earcup may be held onto the patient's ear using a brace that is not connected or otherwise attached to the patient's body. Moreover, the earcup may house a tube or other suitable device that is inserted into the patient's ear. In such an embodiment, vaporized medication may be passed to the patient's ear through the tube.

In an embodiment of the disclosure, the methodologies and techniques described herein are implemented on a special purpose apparatus configured to auricularly deliver medication to a patient's ear. However, the methodologies and techniques may be implemented in other embodiments. The invention has been described herein using specific embodiments for the purposes of illustration only. It will be readily apparent to one of ordinary skill in the art, however, that the principles of the invention can be embodied in other ways. Therefore, this disclosure should not be regarded as being limited in scope to the specific embodiments disclosed herein, but instead as being fully commensurate in scope with the following claims.

I claim:

1. A device comprising:
    an earcup, the earcup comprising a padding configured to form a fluid seal with an ear;
    a drug cartridge or drug reservoir comprising active ingredients; and
    a fluid generator;
    wherein the fluid generator generates a fluid comprising the active ingredients and delivers the fluid to the earcup.

2. The device of claim 1 further comprising a sound emitter configured to deliver sound to the earcup.

3. The device of claim 1, wherein the fluid generator comprises a vaporizer.

4. The device of claim 1, wherein the fluid generator comprises a humidifier.

5. The device of claim 4, wherein the humidifier is selected from the group consisting of: an ultrasonic humidifier, a boiling humidifier, a mechanical humidifier, and a combination thereof.

6. The device of claim 1, wherein the fluid generator comprises a nebulizer.

7. The device of claim 1 further comprising a headband.

8. The device of claim 1 further comprising a controller to control a rate of generation of the fluid by the fluid generator.

9. The device of claim 1, wherein the drug cartridge is replaceable.

10. A system comprising: a headphone comprising at least one earcup, the at least one earcup comprising: a tube; and a padding configured to form a fluid seal with an ear;
    and a replaceable and consumable drug cartridge configured to be coupled to the headphone.

11. The system of claim 10, wherein the headphone further comprises a fluid generator coupled to the drug cartridge, and wherein the fluid generator generates a fluid comprising active ingredients obtained from the drug cartridge.

12. The system of claim 11, wherein the fluid generator comprises a vaporizer.

13. The system of claim 11, wherein the fluid generator comprises a humidifier.

14. The system of claim 13, wherein the humidifier is selected from the group consisting of: an ultrasonic humidifier, a boiling humidifier, a mechanical humidifier, and a combination thereof.

15. The system of claim 11, wherein the fluid generator comprises a nebulizer.

16. A method for auricularly delivering medication comprising:
    receiving, at a fluid generator, medication from a cartridge;
    generating, at the fluid generator, fluid comprising the received medication;
    passing the fluid to an earcup; securing the earcup to an ear to form a fluid seal; and delivering said medication to the ear.

17. The method of claim 16 further comprising a step of placing the earcup adjacent to a patient's ear such that the patient's ear is completely encapsulated by the earcup.

18. The method of claim 16, wherein the fluid generator comprises a vaporizer.

19. The method of claim 16, wherein the fluid generator comprises a humidifier.

20. The method of claim 19, wherein the humidifier is selected from the group consisting of: an ultrasonic humidifier, a boiling humidifier, a mechanical humidifier, and a combination thereof.

21. The method of claim 16, wherein the fluid generator comprises a nebulizer.

22. The method of claim 16 further comprising a step of regulating, at a controller, a rate of generation of the fluid by the fluid generator.

23. The method of claim 16, wherein the medication is passed to the earcup by an impeller.

24. The method of claim 16 further comprising a step of delivering, to the earcup, sound generated from a sound emitter.

25. A method of auricularly receiving medication comprising:
    placing an earcup on an ear to form a fluid seal with the ear, the earcup comprising a tube;
    operating a headphone coupled to the earcup, the headphone comprising a fluid generator; and
    receiving, at the ear, fluid generated by the fluid generator, the fluid comprising active ingredients; wherein the fluid generator receives medication from a cartridge comprising active ingredients.

26. The method of claim 25 further comprising a step of receiving sound from a sound emitter coupled to the headphone.

27. The method of claim 25, wherein the fluid generator comprises a vaporizer.

28. The method of claim 25, wherein the fluid generator comprises a humidifier.

29. The method of claim 28, wherein the humidifier is selected from the group consisting of: an ultrasonic humidifier, a boiling humidifier, a mechanical humidifier, and a combination thereof.

30. The method of claim 25, wherein the headphone further comprises a headband.

31. The method of claim 25 further comprising a step of controlling, at a controller operatively connected to the fluid generator, a rate of generation of the fluid by the fluid generator.

32. The method of claim 25 further comprising a step of coupling, the cartridge to the fluid generator, the earcup, or the headphone.

33. The method of claim 32, wherein the cartridge is detachably coupled to the fluid generator, the earcup, or the headphone.

\* \* \* \* \*